United States Patent [19]

Heilmann et al.

[11] Patent Number: 5,522,724
[45] Date of Patent: Jun. 4, 1996

[54] PROCESS FOR THE MULTI-STAGE TREATMENT OF LUMPY PRODUCTS USING PROCESS MEDIA AND DEVICE FOR CARRYING OUT THE PROCESS

[75] Inventors: Klaus Heilmann; Martin Lauer, both of Wendel, Germany

[73] Assignee: Fresenius AG, Germany

[21] Appl. No.: 267,894

[22] Filed: Jul. 6, 1994

[30] Foreign Application Priority Data

Jul. 6, 1993 [DE] Germany .......................... 43 22 467.9

[51] Int. Cl.$^6$ ..................................................... F27B 9/12
[52] U.S. Cl. .............................. 432/18; 432/43; 432/121; 432/163; 432/207; 34/424; 34/423
[58] Field of Search .................................... 432/18, 43, 52, 432/121, 128, 163, 207; 34/423, 424

[56] References Cited

U.S. PATENT DOCUMENTS

| | | | |
|---|---|---|---|
| 3,197,184 | 7/1965 | Navez et al. .............................. | 432/18 |
| 3,809,529 | 5/1974 | Gornall ..................................... | 432/138 |
| 4,015,935 | 4/1977 | Andersson et al. ............................ | 21/2 |
| 4,094,633 | 6/1978 | Peterson et al. ........................ | 432/118 |
| 4,496,312 | 1/1985 | Yamada et al. ............................ | 432/11 |
| 4,906,183 | 3/1990 | Kyffin et al. ............................ | 432/138 |
| 4,966,547 | 10/1990 | Okuyama et al. .......................... | 432/9 |

FOREIGN PATENT DOCUMENTS

| | | |
|---|---|---|
| 0333389A1 | 9/1989 | European Pat. Off. . |
| 0427323A1 | 5/1991 | European Pat. Off. . |

*Primary Examiner*—Henry A. Bennett
*Assistant Examiner*—Siddharth Ohri
*Attorney, Agent, or Firm*—Sterne, Kessler, Goldstein & Fox

[57] ABSTRACT

Process and device for the treatment of lumpy products using process media, the treatment including a predetermined sequence of process steps. A chain of treatment units is moved in a stepwise manner. The product to be treated remains within the same treatment unit for the duration of the sequence of the process steps. A supply unit supplies and removes process media in a stopping-station specific manner so that the process steps can proceed simultaneously in the treatment units.

22 Claims, 5 Drawing Sheets

PROCESS FOR THE MULTI-STAGE TREATMENT OF LUMPY PRODUCTS USING PROCESS MEDIA AND DEVICE FOR CARRYING OUT THE PROCESS

DESCRIPTION

The invention relates to a process for the treatment of lumpy products using process media within the framework of a sequence of process steps (treatment stages) in a treatment unit. It also relates to a suitable device for the treatment of lumpy products using process media removable from a supply unit, within the framework of a sequence of process steps (treatment stages) in a treatment unit.

Such a process, including the associated device is known from EP-A1 0 333 389.

This prior art describes a so-called large-capacity autoclave which is used to carry out most treatment processes in which underpressure and harmful media prevail.

This large-capacity autoclave has a relatively large sealable chamber into which the products to be treated are introduced in batches.

In the chamber, the different treatment processes with their characteristic parameters such as type of medium, through-flow, temperature and pressure are then carried out in chronological succession in the chamber on all the products in the chamber at the same time.

The larger such single-chamber autoclaves, which are worked according to the batch process, are built, the more favourable are they as regards procurement and operation. In the case of procurement, because enlargement of the chamber and of the assemblies is cheaper than the realization of several smaller autoclave units; in the case of operation, because with thermal polarity-inversion processes, the unit mass also to be subjected to polarity-inversion is greater for several small autoclaves than for one large autoclave. Further, with the degree of automation usual today, the organisation and personnel expenditure is greater for several small autoclaves than for the large-capacity autoclave.

The large-capacity autoclave has several serious disadvantages.

1. The uniformity of the treatment between the products which were treated in one chamber, i.e the product quality, generally becomes lower the more products pass into the chamber, i.e. are autoclaved in one cycle. Because of the multitude of products, the uniformity of the temperature and pressure conditions within the chamber can no longer be guaranteed. The superiority of the large-capacity autoclaves as regards procurement is based however merely on allowing the space which is available to the products and the media guide cross-sections to increase to a lesser extent than would be the case if several small autoclaves were used to achieve the same productivity. The lower uniformity makes over-sizing of the treatment process necessary in order to avoid too large a quantity of rejects; this in turn impairs the product quality, the productivity and the energy consumption and raises the expenditure for regular quality checks.

2. The high number of products to be treated simultaneously in the chamber of the large-capacity autoclave to be treated simultaneously means that correspondingly large-dimensioned buffer stores have to be installed and operated in front of and behind the autoclave unit. The expenditure for a fully-automated operation of these stores is considerable.

3. Because of the charge or batch operation, no autoclaving is possible during feeding and during cooling and unloading of the treated products. The effectiveness of such a large-capacity autoclave unit therefore becomes smaller with a large number of products.

In order to circumvent these problems, there has been a switch, especially in the case of foods or infusion bottles, to continuous treatment in through-line operation, especially to sterilization. These sterilisation processes are described in a series of patent specifications and literature sources, representative reference being made to U.S. Pat. No. 4,094,633, EP A1 0 427 323 and the book by Wallhäuser, Praxis der Sterilisation (pages 242/243).

Common to all the processes is the sterilisation of the products passing through a space (heating chamber) which contains the sterilising medium (e.g. steam). Such a plant is to be operated under pressure only if the heating chamber is fitted with sluices or valves, as described in U.S. Pat. No. 4,094,633.

In most cases, the continuous plants operate according to a 3-phase system: preheating—sterilising—cooling, the individual operations proceeding as a rule in separate, fixed chambers which are connected to each other, which can be arranged in the form of a tower, i.e. each product flows in chronological succession through each treatment stage in a different chamber (treatment unit).

All continuous plants have the disadvantage that they are very specialised in the product. Since they are supplied automatically for reasons of profitability, this feed plant is likewise designed specially for the autoclave. A plant of this type is for example described in U.S. Pat. No. 4,015,935.

Another disadvantage is that the same sterilisation medium must always be used in such a unit.

Another multi-chamber system has become known from DE 35 07 337 C2. This shows a process and an associated device for the coating of substrates within the framework of a sequence of process steps. For each process step (treatment stage) a group of treatment containers is provided which can be arranged both linearly and circularly. By means of a transport system which has a transport chamber with sluice, the substrates are sluiced after treatment with the process step "n", out of the container of the associated group into the transportation chamber and sluiced from there into a container of the group which is allocated to process step "n+1".

With this system, the different process steps therefore take place in different chambers, the goods to be treated being transported from chamber to chamber, in contrast to the autoclave technique where the product remains in the chamber and is there subjected to the individual process steps in succession.

The known system therefore requires a transport and sluice system which is costly in terms of time and material. It is also designed especially for the coating of substrates.

It is the object of the invention to develop the process described at the beginning and the corresponding device such that—whilst maintaining the batch operation mode—the product quality is improved, buffer stores are largely superfluous and, despite retaining the batch operation mode, a quasi-continuous treatment is possible.

This object is achieved for the process by the fact that there is formed as treatment unit a chain of at least three separate single treatment units in which the lumpy products remain for the duration of the sequence of process steps, that in the chain, divided among the single treatment units, the individual process steps of the sequence take place simultaneously, that the sequence of process steps in the single treatment units of the chain or in groups thereof begins in a pre-set cycle with a time stagger, and that the time stagger (cycle) is pre-set by a common control and regulating unit.

As regards the device, the object is achieved by the fact that the treatment unit consists of a plurality of at least three separate single treatment units, each of which has an inlet and outlet for the process media, and in which the lumpy products remain for the duration of the sequence of process steps, that the inlet and outlet of the single treatment units are connected to the supply unit such that in the chain, divided among the individual single treatment units, the individual process steps of the sequence proceed simultaneously, that a common control and regulating unit is provided which is constructed and connected to the single treatment units in such a manner that the sequence of process steps starts in the single treatment units of the chain and groups thereof in a pre-given cycle at staggered times.

The single treatment unit can be formed by:

a chamber with piece goods, a chamber with a small charge, a individual item to be treated which (without surrounding chamber wall) is secured with connector contacts.

The common control unit is preferably formed mechanically in the form of a transport system for the single treatment units which transports the single treatment units to different places, in which at least one treatment stage is carried out in each case, and the start of treatment is determined by the place of the corresponding chamber or a timed driving arrangement is allotted to the treatment units as common control unit for producing a stepwise movement of the single treatment units with a characteristic number of stopping stations, in which specific treatment steps take place, whereby connection systems for the process media are provided which are firmly connected on the one side to a fixed supply unit and which on the other side can be brought into active engagement with the inlet and outlet of the single treatment units in stopping station-specific manner, so that the single treatment units in the stopping stations are impingable by the fixed supply unit in position-dependent manner with the process media necessary for the corresponding treatment stage.

With the preferred system according to the invention, a single treatment unit is initially formed in the first stopping station, for example a certain quantity of products to be treated is enclosed in a first single chamber. Afterwards, this single unit, for example the single chamber, travels to the next (second) stopping station where the next process step is also carried out, for example "preheating". At the same time, the contents of the next single unit are unloaded at the first stopping station and new product is loaded. In the next time cycle the said first single unit travels to the next, third, stopping station, the second single unit to the second stopping station etc. After the passage through is complete, the treated product can be removed.

With the system according to the invention, the products are accommodated in many small single treatment units during their treatment, i.e. correspondingly fewer products go to one single unit than comparatively with single-compartment large-capacity autoclaves. Treatment occurs in each single unit as before according to the aforementioned batch process, but for the totality of the single units there results the continuous shift register process, and for the media supply assemblies even a quasi fully-continuous method of operation.

The products enter the device individually and regularly and leave it with the same frequency after treatment. As the products are preferably in sealable chambers during their treatment, treatment processes can be used which require sealablitity relative to the plant environment. These processes include for example treatments at under- or overpressure or treatments with media which must not escape into the environment.

This process has the following advantages:

The required product buffers are smaller by at least the factor which corresponds to the number of single treatment units, in particular the single chambers, compared with an equally productive large-capacity autoclave.

The number of products which are treated together as a batch in a single chamber is reduced compared with the large-capacity autoclave. The uniformity of the media flow guide relative to the products, i.e. generally the reproducibility of the physical conditions in the single autoclave chamber is therefore in principle higher than with large-capacity autoclaves. Smaller over-sizings of the treatment process and therefore increased productivity with improved product quality thus result.

Effectiveness becomes greater since there is no loss of work rate when the charges are inserted and removed. At the same time, there is no loss of space such as in the not fully filled large-capacity autoclave.

Whilst, in large-capacity autoclaves, the treatment sections take place individually and with a time stagger, with the invention all treatment sections take place continually and simultaneously, but with a time stagger. Since the associated assemblies in the supply unit are operated continuously, they turn out to be smaller and cheaper than in the case of large-capacity autoclaves, where the assemblies always have to be operated only for a time, but then at a higher output. For the same expenditure on control engineering, the continuously-operated assemblies work more uniformly and reproducibly in the case of the invention than the discontinuously-operated assemblies of the large-capacity autoclave.

An important further advantage of the invention is that, for a comparable technical outlay, energy consumption can be substantially reduced in process-dependent manner compared with the large-capacity autoclave. This depends inter alia on the smaller assemblies operated continuously at the optimum degree of efficiency.

Another advantage is the increased productivity at uniform operation.

By virtue of the fact that the products can be introduced into the plant and removed again individually and uniformly, it is possible to integrate the device according to the invention into a production line without buffer, for example between assembly and packing.

An important advantage of the invention is the practical realizability of the partial energy recovery during treatment procedures which include cooling and heating-up processes. The cooling media heat up upon cooling of the products, chambers and pipelines, and can be continuously used at another treatment station to heat up the products. With large-capacity autoclaves, the heating-up and cooling down processes are however at separate times from one another and large quantities of media and energy would have to be stored until they are used again, which would result in correspondingly higher investment costs for the plant.

In the case of incidents which affect the individual single treatment unit, for example a chamber, for example a door becoming leaky, it is possible without great expenditure in terms of control to exclude the affected chamber from the cycle of chambers filled with products until the damage has been dealt with. Thus, it is not essential that the plant be stopped in the case of such incidents and only the products from the defective single chamber are rejected where necessary.

In the case of incidents which affect individual assemblies, for example the breakdown of a fan, only those products which still have to undergo treatment with this defective fan may be rejected; the other products can be treated properly to the end and removed from the plant. However, since in most cases an assembly becomes defective during its start-up phase, all the products in the chamber are rejected as a rule, on the other hand, in the case of large-capacity autoclaves.

The continuity of the process is further increased until the buffers are done away with completely by virtue of the fact that handling machines remove the products individually or in small groups from the chamber which has just opened or introduce them into it and that these products enter and leave the autoclave plants at still further reduced time intervals and in singularized form on transport devices. Since the products to be treated are lumpy in shape anyway, i.e. arrive piece for piece from the upstream manufacturing section and are used analogously piece for piece in the downstream manufacturing section, the autoclave plant according to the invention can rightly be described as a continuous autoclave as regards the lumpy products.

Compared with the known continuous autoclaves, the versatility of use is also advantageous. Since each product (or a small product range) is accommodated in a replaceable single treatment unit, for example a chamber, it is possible to simultaneously sterilize different products in different chambers (regardless of whether they are liquid, solid, granulated, open, packed etc.). Different treatment, in particular sterilisation, media can also be fed to each chamber in the same cycle, since each chamber has its own feed line. For example, one chamber can be rinsed thoroughly with hot steam, but a following one e.g. with aqueous citric acid. Nevertheless, the whole plant does not have to be switched over to the other sterilisation medium. Other procedures can also be connected, e.g. pickling, coating, purifying etc.

The invention provides a large application range for the treatable products.

The products which can be treated in the plant must exist in a form or be able to be converted into such a form which makes it possible to introduce them into the chambers using suitable handling devices and to remove them after their treatment. This requirement can be met for almost all products; examples: liquid or granular products in closed or open, rigid or flexible containers, products which are mechanically unstable or difficult to handle in product racks or in half-open, porous or closed packages.

In many instances the suitable packing container for the product is not only a prerequisite for their handling properties, but an essential constituent of the treatment process; example: sterilisation of medical tube systems in sterilization vapour-permeable and at the same time bacteria-impermeable membrane packing.

In other cases, the product or its packing itself already represents a sealable container, that is to say an autoclave, in which the treatment process can be carried out; example: a haemodialysis filter is a container which can be sterilised using through-flowing steam. In these cases, according to a development of the invention product-accommodating chambers are replaced by connection devices to the products. With products which are acted upon internally with media during their treatment, these connecting devices can for example be pipeline couplings. The connection devices can however also for example be heat exchangers coupled externally to the product surface.

The application range is also considerably large as regards the applicable treatment process.

The invention allows each single treatment unit, for example individual chamber, to be acted upon with different media according to the same program and with high reproducibility.

These media can be used to influence the products directly or indirectly; examples: direct effect of bacteria-killing gases, direct effect of drying hot air, indirect effect through saturated steam which heats through at the surface of the product package, indirect effect through heated pipe-coils, which for example transfer radiant heat to the product under vacuum conditions.

Some examples of applicable treatment processes are listed in the following:
  drying processes (vacuum, radiant heat, hot air . . . )
  sterilisation processes (moist/dry heat, sterilising gases)
  thermal processes (boiling, baking, curing) other processes such as pickling, coating, purifying . . .

A particularly favourable construction of the device results if the single treatment units, in particular the individual chambers, are constructed in the same manner. This also eases the maintenance of the plant and reduces the production costs.

In principle, the single treatment units, for example the individual chambers, can be moved in a linear chain, the chamber which has proceeded through the last treatment step returning rapidly to the starting point. It is expedient to provide an additional individual chamber and to bring this in each case to a parking position at the starting point, in order to be able to couple it immediately into the chain, before the returning chamber is at the starting point, which for in turn then assumes the parking position.

According to one embodiment of the invention it is however particularly advantageous if the single treatment units, for example the individual chambers, are arranged in a circular ring and the phased driving arrangement has a rotating drive, i.e. in accordance with the process the product to be treated is transported circularly with its single unit.

Through this, the space requirement becomes relatively small. A uniform cyclical movement pattern is also achieved by the rotary movement then taking place, which also permits a better supply of the moved individual chambers with the treating flowing media out from the centre of the rotational movement using a new type of through-feeding.

Also conceivable however is the construction of a chain of single treatment units which are arranged in stationary manner, the chronological treatment process of which is determined in place-specific manner by a common control unit, whereby operating personnel pass by the chain in order to load and unload the individual units in question.

Other designed features, advantages and application possibilities of the invention can be seen with reference to embodiments of the invention shown in the drawings.

Figure 1:
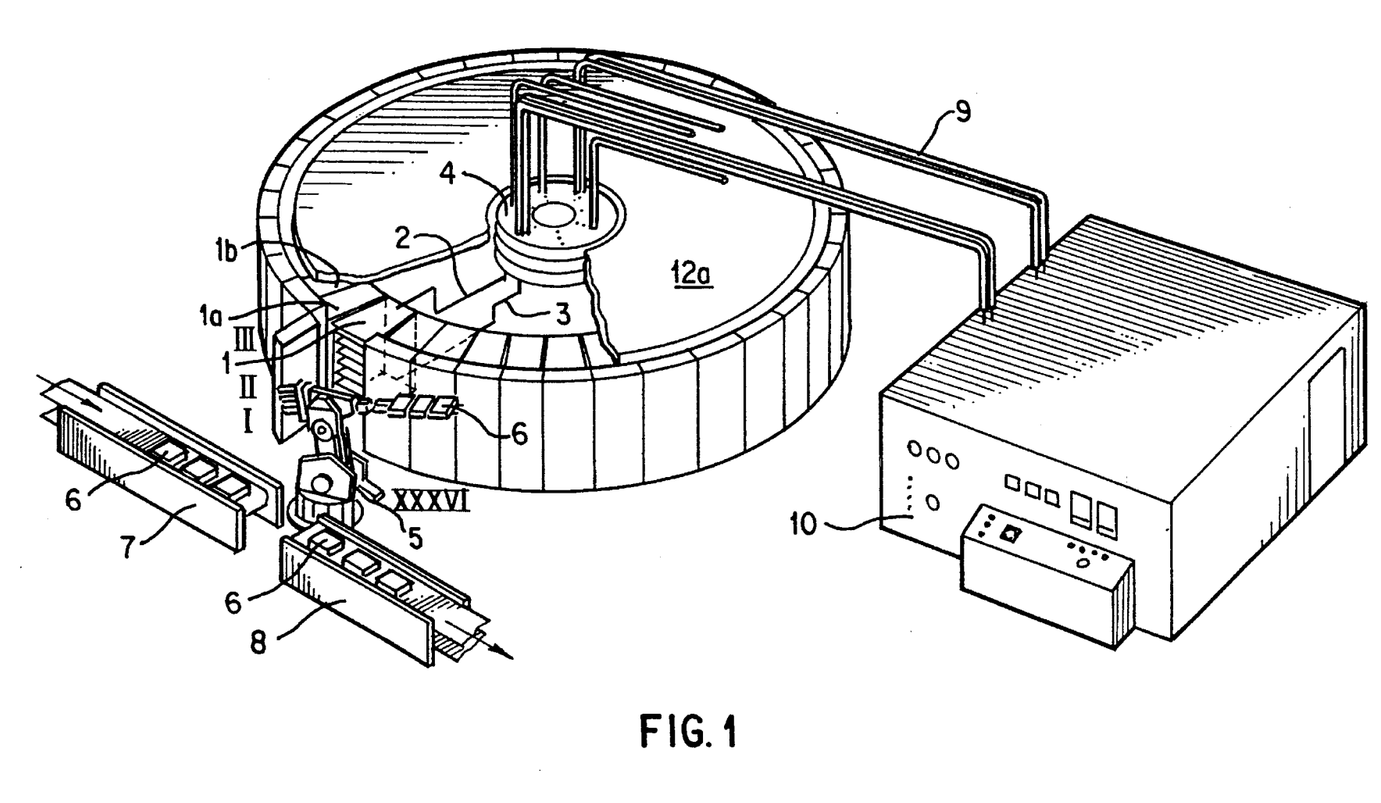
FIG. 1 in diagrammatic, perspective representation, an overall view of an advantageous, preferred embodiment of the device according to the invention with single chambers as single treatment units which are arranged in the form of a circular ring.

These show:

FIG. 1 shows an autoclave device for the multi-stage treatment of lumpy products using flowing media.

The autoclave consists of a plurality of single chambers 1, 1a, 1b etc., 36 chambers being provided in the present embodiment. The number of chambers is determined inter alia according to the number of treatment steps, the necessary buffering, the number of cycles, the space available etc.

The single chambers are arranged in the form of a circular ring on a rotating mount and are moved in steps, i.e. in each case by one chamber breadth (1/36th revolution), as is explained in more detail with reference to FIG. 2.

Each single chamber is an essentially rectangular pressure container with tightly sealable door 17. The principle of the structure of the single chambers is to be explored in more depth with reference to FIGS. 3 and 4. Each single chamber has an inlet and outlet 2, 3 for the process media and the pressure and underpressure production, which are led to a central rotary feed system 4, the structure of which is described in more detail with reference to FIG. 5.

A stopping station is allotted to each chamber place, i.e. to each chamber position, in which position-specific process sequences take place. In FIG. 1 the charging and emptying of the chamber is allocated to the stopping station I in which single chamber 1 is positioned. A mechanism (not shown) installed in fixed manner takes over the automatic opening and closing of the chamber door. A standard commercial handling device 5 in the form of an industrial robot is also allocated to the stopping station I, the loading station, for the batchwise loading and unloading of the products 6 into the corresponding single chamber positioned in the stopping station I, in FIG. 1 into chamber 1.

The treatment cycle starts and finishes at the loading station with the charging and emptying of the products, whereby a plant can have several such stopping stations. A transport device 7 brings the products to be treated 6 from the outer region of the plant to the loading station, whilst a transport device 8 conveys the treated products from the area of the plant.

When charging the single chamber, the handling device 5 removes the products 6 singly or in small groups (in Example 3) from the transport device 7 and transfers the products 6 to the transport device 8 in the same way on unloading.

Loading and unloading can naturally also be carried out manually.

If loading and unloading are carried out during the course of the treatment step which takes the longest time, i.e. of the cycle, there is continuous operation of the autoclave plant overall.

In each of the other stopping stations II, III etc. to XXXVI the chamber doors remain closed and the single chambers are acted upon by various process media in position—i.e. stopping station-specific manner via the rotary feed system 4 and connection systems 9 from a fixed supply unit 10.

The supply unit combines the media periphery and control system in a common housing.

The media periphery includes all necessary assemblies for the working up and distribution of the process and auxiliary media between the media lines of the internal mains supply and the media lines to the rotary feed system.

The term control covers all devices for process control, for the switching of electrical and control-pneumatic consumers, sensors, evaluation and regulation devices, operating software, plant cabling and a control panel with its switches, display devices and recorders.

The supply unit 10 and the connection systems 9 are made from known materials and can be constructed and connected in the usual way by a process engineering specialist without further information.

The assemblies of the supply unit operate continuously. The scheduled impingement of the chambers with the correct medium takes place via the rotary feed system 4. It effects the transfer of the media from the fixed supply unit 10 or from the connection system 9 connected firmly thereto to the rotating single chambers. The rotary feed system basically consists, as FIG. 5 in particular shows, of two parts, namely a rotor in the form of a sliding disk 23 which is rigidly connected via lines 2, 3 to the single chambers 1, 1a etc. and rotates together with them, and a stator in the form of sliding rings 24 which are connected firmly to the connection systems 9, i.e. are fixed.

The sliding disk (the rotor) has a hole for the connections 2 and 3 of each single chamber, via which the media can flow into and out from the chamber. The sliding rings (the stator) have one or more oblong-hole zones 25 for each process medium connection of the connection systems 9 (FIG. 7) in order to create a free passage to the holes in the rotating sliding disk for the passage of the process medium. The position of the holes and of the oblong-hole zones is selected such that each single chamber is supplied in the stopping station in question with the process media required there or is activated in the required manner.

The rotary feed system thus structurally contains the media switch program, control with valves being largely unnecessary.

Because the functions of chronological and circuit-based media control have been taken over by the rotary feed system, the expenditure on the control turns out to be less, relative to the size of the plant, than in the average for plants.

The wiring of the media lines between the connection pieces of the rotary feed system and the pipelines to the supply unit expediently takes place in the manner of a points switch. Should several single chambers be connected in series in specific angle of rotation ranges, pipe bends are laid from the connection pieces of the chamber outlets to the connecting pieces of the neighbouring chamber inlets; if, on the other hand, several chambers are to be flowed through in parallel, several connecting pieces are brought together in each case and connected to a main media line.

Figure 2:
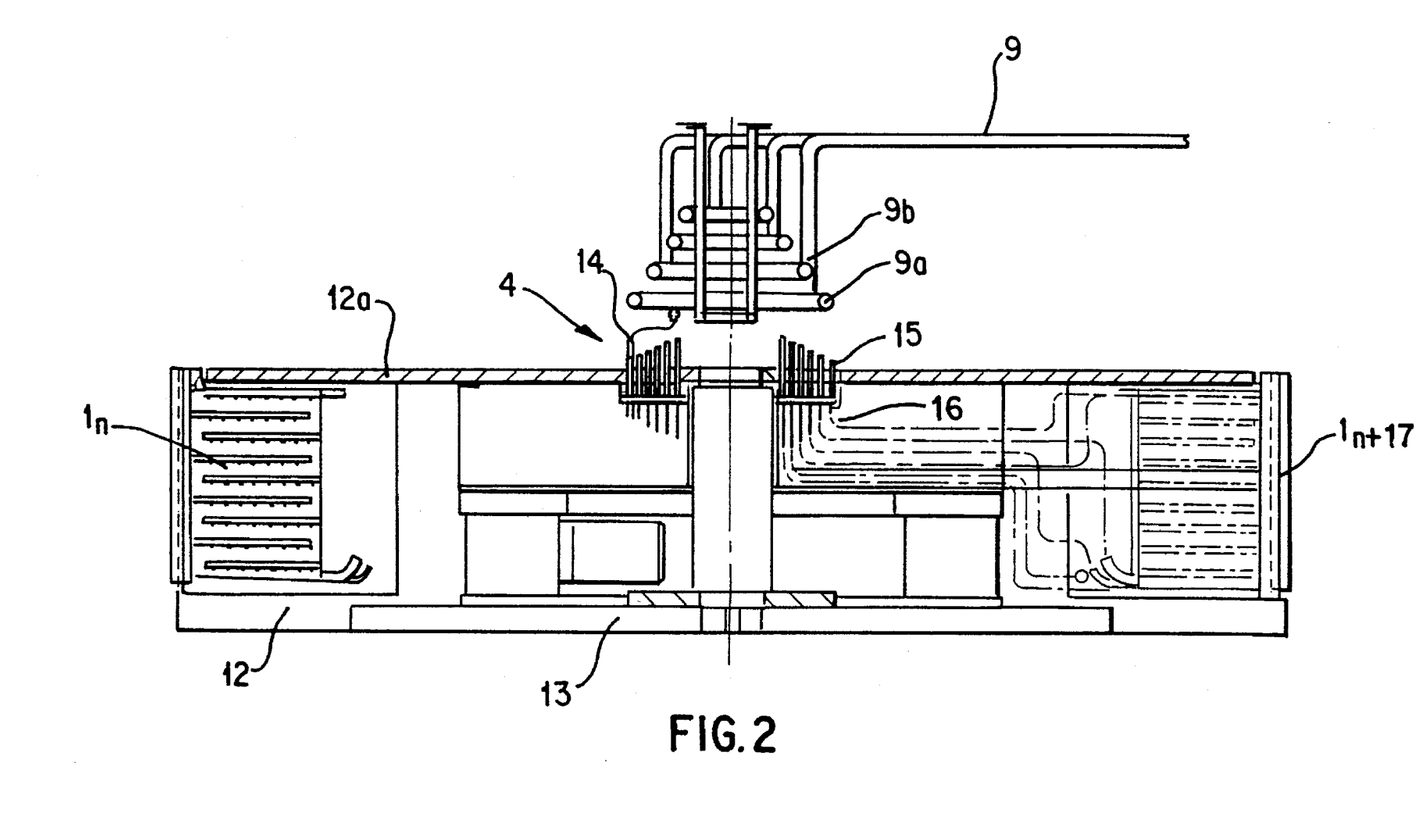
FIG. 2 a longitudinal section through the circular ring of the single chambers of the device according to FIG. 1.

FIG. 2 shows a section through the circular chamber arrangement according to FIG. 1 at an arbitrary position, i.e. through the single chamber 1n and the single chamber $1_{n+17}$ lying opposite. The single chambers rest on a rotary mount 12 which is supported and moved by the circular cycle drive in the form of a circular switch panel 13. Such circular switch panels are commercially available and ensure the necessary cycle times and the required divisional accuracy when the single chambers move in stepwise manner.

The entire internal space of the circular ring is provided with a cover 12a (see also FIG. 1), firstly to give the plant a closed external appearance and secondly to protect the plant components.

The lines of the connection systems 9 open out into ring circuits 9a, 9b etc., which for their part are connected via hoselines 14 and connection pieces 15 to the sliding rings of the rotary feed system 4. The connections of the chambers are led for their part to connecting pieces 16 which are attached to the rotor of the rotary feed system or to the holes therein. This line routing is shown diagrammatically in the right-hand part of FIG. 2.

The types of connection shown are only examples. Very many possibilities and sub-variants are available to the specialist.

Figure 3:
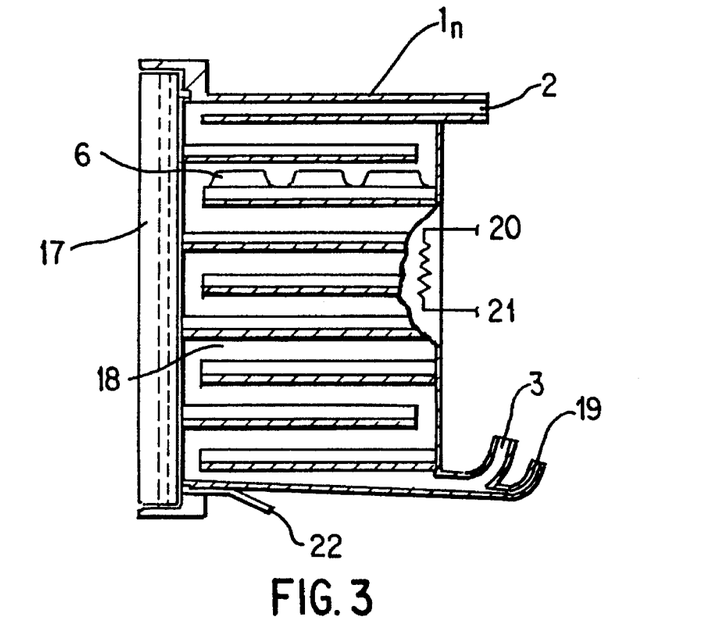
FIG. 3 a longitudinal section through a single chamber of the device according to FIG. 1.
Figure 4:
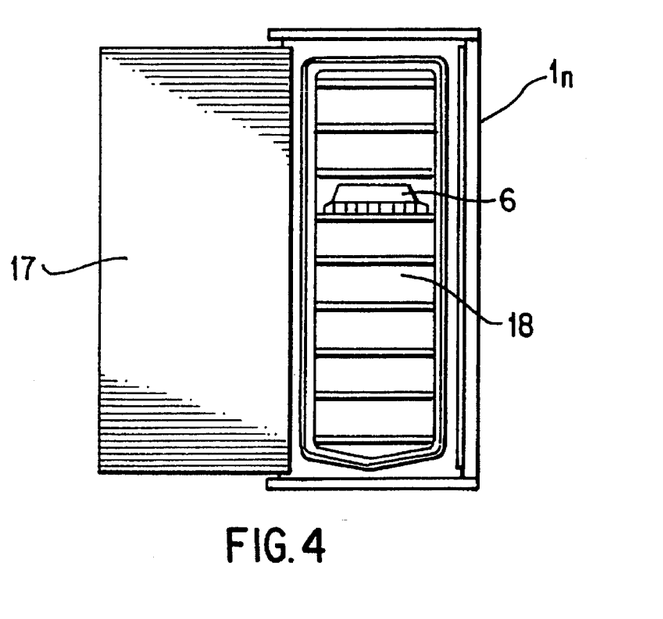
FIG. 4 a front view of a single chamber with opened door.

FIGS. 3 and 4 show as embodiment details in the structure of the single chambers which are preferably constructed in the same way. FIG. 3 shows a longitudinal section through the single chamber $1_n$ with closed door 17, whilst FIG. 4 shows a front view with opened door. Each single chamber represents an essentially rectangular pressure container with tightly sealable door. The inner space of the single chamber is sub-divided into compartments 18, a ribbed sheet lying on each compartment floor. The products 6, of which a group of three is shown, lie on the ribbed sheet. The ribbed sheets are arranged alternately offset from compartment to compartment (see FIG. 3) and thereby cause the process media to flow in a meandering stream and the process media to flow round all sides of the products. The ribbed sheets also permit the products to be loaded into and unloaded from the compartments using fork-shaped grippers.

For the design of door, door frame, door closure and door seal, there is a series of possibilities, e.g. trap door designs or sliding doors with opening direction upwards, available to the specialist.

The type of construction of the door operating mechanism results for the specialist from the chosen type of construction of the doors.

Each single chamber has connections 2, 3, 19–22, which, as FIG. 2 (in conjunction with FIG. 5) shows diagrammatically, are guided against the sliding disk 23 of the rotary feed system 4. The two large connections 2 and 3 serve as process connections for the process media. The small process connection 19 has the task of removing chamber condensation. Connections 20 and 21 supply the pipe-coil heating systems of the individual compartments with heating steam and remove the condensation produced. Connection 22 ensures operation of the door, for example by compressed air.

Figure 5:
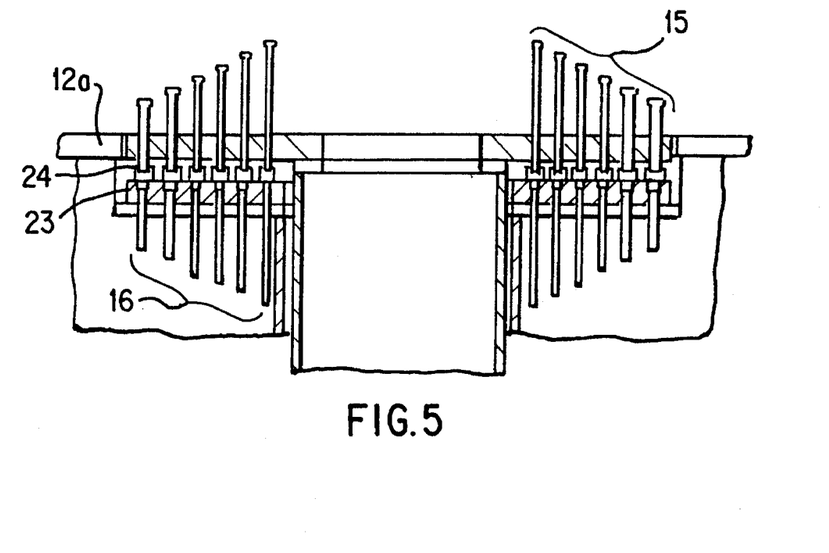
FIG. 5 an enlarged cut-out section from FIG. 2 in the region of the rotary feed system.
Figure 6:
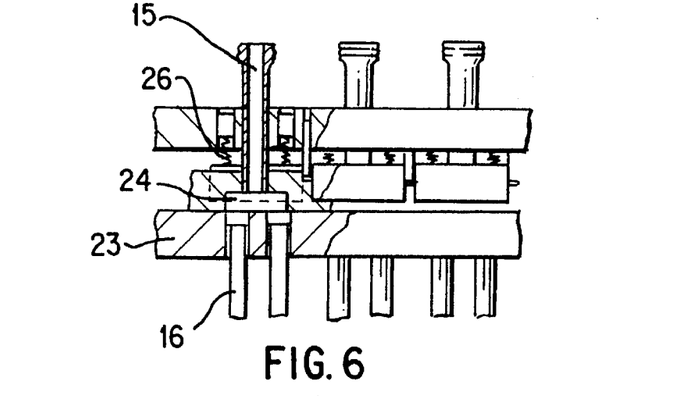
FIG. 6 an enlarged cut-out section from FIG. 5 in the sliding area of the rotary feed system.
Figure 7:
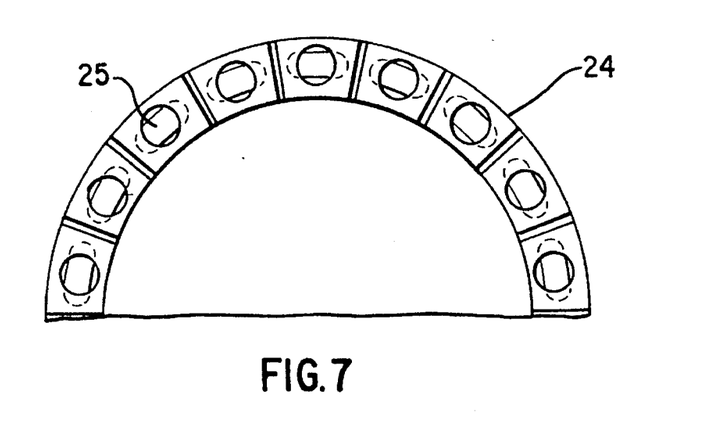
FIG. 7 a top view of the stator of the rotary feed system.

FIGS. 5–7 show details of the rotary feed system 4 of FIGS. 1 and 2. FIG. 5 represents an enlarged section through the (upper) centre of FIG. 2. FIG. 6 is an enlarged cut-out section from FIG. 5 in the region of the cooperation between rotor and stator of the rotary feed system.

FIG. 7 again shows a top view of a sliding ring of the stator.

The connecting pieces 16, to which the connections of the single chambers (FIG. 3) are guided (see also FIG. 2, right-hand part), open out into the sliding disk 23 or into the bores therein. The connecting pieces 15, which according to FIG. 2 are connected via hoselines 14 to the ring circuits $9a$ et seq. of the connection systems 9, open out into sliding rings 24 or into oblong-hole zones 25 therein, which are to be recognized particularly well from FIG. 7 in the top view of a sliding ring. Components 26 pre-tensioned by springs ensure the necessary contact pressure of the rotor at the stator, so that the process media cannot escape at the side. It is thereby expedient to provide sealing systems in this sliding region, for which many possibilities are open to the specialist.

Figure 8:
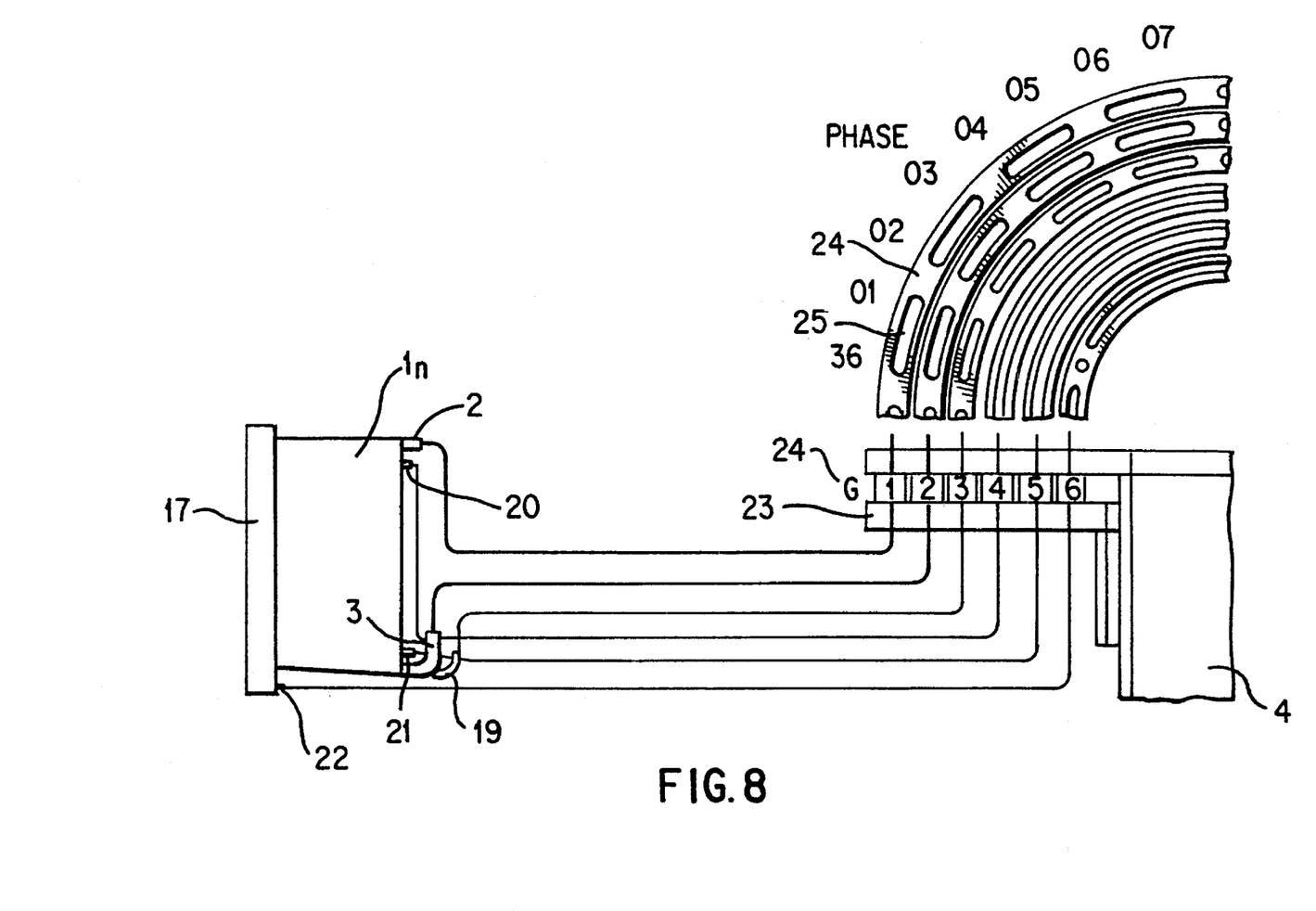
FIG. 8 in diagrammatic representation the spatial program circuit diagram in the rotary feed system.

To explain in more detail the "wiring" of the chambers to the connection systems 9 via the rotary feed system, FIG. 8 shows a "wiring diagram" for the process described in the following table. FIG. 8 shows a single chamber $1_n$ with door 17 and connections 2, 3 and 19–22 (see FIG. 3), which are tightly connected to the sliding plate 23. Six sliding rings 24 are shown, numbered G1–G6. In the upper part of FIG. 8, these sliding rings are quasi tilting upwards with their oblong-hole zones 25 as top view, with the allocation of the individual oblong-hole zones to the treatment steps, called phases. In the end, these phases also correspond to the individual stopping stations.

TABLE

| Section | | Sliding rings | | | Media, through-flow, state | | |
|---|---|---|---|---|---|---|---|
| Phase | Processes | G1 | G2 | G3 | G4 | G5 | G6 |
| 01 | Cool Load/unload | Atmospheric air with compressed air | | | Heating steam | Condensate | Vacuum |
| 02 | Dry | Hot air | | | " | " | compressed air |
| 03 | Heat | | | | | | |
| 04 | Vent | Vacuum | | blocked | " | " | " |
| 05 | | | | | | | |
| 06 | Heat and moisten | Pure steam Vacuum | | blocked | " | " | " |
| 13 | | | | | | | |
| 14 | Sterilize | Pure steam | | condensate and residual pure steam | " | " | " |
| 25 | | | | | | | |
| 26 | Dry | Hot air Vacuum | | | " | " | " |
| 35 | | | | | | | |
| 36 | Dry ventilation Cool | Compressed air | | | " | " | " |

The table shows in the first column the phases, corresponding overall to the chamber number of 36 phases selected in the embodiment. The second column shows which treatment or process steps are allocated to the individual phases. It can be deduced from the other columns which process media flow during the individual process steps over the oblong-hole zones of the sliding rings—and therefore corresponding to FIG. 8—into the associated connections of the single chambers.

Thus, a vacuum is produced in phase 01, i.e. in the loading station I (see FIG. 1) via the sliding ring 6 at the connection 22 (see FIG. 8), i.e. the chamber door 17 opens. At the same time, atmospheric air with compressed air flows in via the sliding rings G1–G3, i.e. into the chamber connections 2, 3 and 19, and out. Heating steam is connected to the connection 20 of the pipe-coil heating via sliding ring G4; the condensate is removed via the connection 21 and the sliding ring G5.

In the second phase, that is when the single chambers have moved by one step, the drying and heating of the products and the chamber takes place (in the considered chamber), with hot air which is fed in and removed via sliding rings G1–G3. The pipe-coil heating is also charged via the sliding rings G4 and G5. The chamber door is closed in this phase, since compressed air is present at the door connecting pieces 22 via the sliding ring G6. These processes are repeated when the chambers are again rotated by one step into phase 3, i.e. the corresponding process step is distributed over two chamber steps. The other phases proceed accordingly until finally the end of the cycle is reached with phase 36, the "dry ventilation and cooling", and the products are ready to be unloaded.

In a particularly advantageous embodiment, the device according to FIG. 1 has not only replaceable chambers, but connector contacts, with the result that during a sterilisation process e.g. dialyzers can be connected and chambers with hose system packages. The use possibility is universal due to the all-round nature of the connection possibilities.

We claim:

1. Process for the treatment of lumpy products using process media, the treatment including a predetermined sequence of individual process steps, comprising:

forming a treatment chain comprising a plurality of separate treatment units for each receiving therein lumpy products, said plurality determined by the individual process steps, wherein lumpy products remain in the same treatment unit for the duration of the entire treatment; and simultaneously performing the individual process steps in said plurality of treatment units, wherein the individual process steps are time-staggered by a cycle period, said cycle period being preset by a common control and regulating unit.

2. Device for the treatment of lumpy products using process media, the treatment including a predetermined sequence of individual process steps, comprising:

a treatment chain comprising a plurality of separate treatment units for each receiving therein lumpy products, said plurality determined by the individual process steps, wherein lumpy products remain in the same treatment unit for the duration of the entire treatment, each of said treatment units having an inlet and an outlet for the process media;

a supply unit for supplying and removing the process media connected to said treatment units so that the predetermined sequence of individual process steps can proceed simultaneously in said treatment units; and a common control and regulating unit connected to said treatment units, said common control and regulating unit configured so that the start of the predetermined sequence of individual process steps for each of said treatment units is time-staggered.

3. Device for the treatment of lumpy products using process media, the treatment including a predetermined sequence of individual process steps, comprising:

a treatment chain comprising a plurality of separate treatment units for each receiving therein lumpy products, said plurality determined by the individual process steps, wherein lumpy products remain in the same treatment unit for the duration of the entire treatment, each of said treatment units having an inlet and an outlet for the process media;

a supply unit for supplying the process media connected to each of said treatment units so that the predetermined sequence of individual process steps can proceed simultaneously in said treatment units;

a common control and regulating unit connected to said treatment units, said common control and regulating unit configured so that the start of the predetermined sequence of individual process steps for each of said treatment units is time-staggered, wherein said common control and regulating unit comprises a timed drive arrangement to produce a stepwise movement of said treatment units, and with a characteristic number of stopping stations at which specific individual process steps take place; and connection means for providing and removing the process media, one side of said connection means connected to said supply unit, the other side of said connection means configured to be brought into active engagement with said inlet and said outlet of said treatment units in stopping station-specific manner, so that said treatment units in the stopping stations are impingable in position dependent manner by the process media necessary for the specific individual process step for the stopping station concerned.

4. Process according to claim 1, wherein said common control and regulating unit is mechanically formed in the form of a transport system for said treatment units, which transports said treatment units to different treatment sites at which at least one individual process step is carried out, wherein the start of the treatment is determined by the treatment site of the corresponding treatment unit.

5. Process according to claim 1, wherein said treatment units remain in essentially the same site during the treatment and the start of the treatment for each of said treatment units is pre-set by said common control and regulating unit, wherein said common control and regulating unit controls the flow of the process media.

6. Process according to claim 1, wherein said treatment units are further transported during the treatment and the time stagger of the start of the treatment is determined by said common control and regulating unit which controls the flow of the process media.

7. Process according to claim 4, wherein said treatment units are transported one after the other in stepwise manner to the treatment sites, and wherein said chain of treatment units is formed by loading a new unit in each case when the preceding, loaded treatment unit is transported into the next treatment site and a treated treatment unit is unloaded when the next treatment unit has been transported to the last treatment site according to the last individual process step.

8. Process according to claim 4 or 7, wherein said treatment units are transported in a circular path.

9. Process according to claim 7, wherein said at least one individual process step includes several transportation steps.

10. Process according to claim 1, wherein individual process steps in which the lumpy product is cooled using a cooling medium, the heated cooling medium is returned to another individual process step as process medium for the heating of the lumpy products in another treatment unit, for the purpose of partial energy recovery.

11. Device according to claim 3, wherein at least one stopping station is provided for the loading and unloading of said treatment units with the products for treatment and wherein at least one handling device is allocated to said at least one stopping station for the loading and unloading of the lumpy products for treatment into the treatment unit positioned in said at least one stopping station.

12. Device according to claim 11, further comprising feed and removal transport devices allocated to the handling device.

13. Device according to claim 11, wherein said treatment units are formed by single chambers, loadable with piece goods or a small charge.

14. Device according to claim 13, wherein said single chambers are constructed in the same way.

15. Device according to claim 13 or 14, wherein said single chambers are designed as rectangular pressure containers with a tightly sealable door.

16. Device according to claim 13, wherein said single chambers have an opening and closing mechanism which can be activated automatically in said at least one stopping station.

17. Device according to claim 3, wherein a holder with connector connections is provided as at least one of said plurality of treatment units, which connections are designed to accommodate products, compression-resistant in themselves, which are to be treated on the inside and can be brought into active engagement with said connection means.

18. Device according to claim 3, wherein said treatment units are arranged in the shape of a circular ring and said timed drive arrangement has a rotating drive system.

19. Device according to claim 18, wherein said treatment units are mounted on a rotating mount.

20. Device according to claim 19, wherein said rotating mount is secured to a circular switch panel.

21. Device according to claim 18, further comprising a rotary feed system provided for the position-dependent impingement of said treatment units by process media, which firstly has a stator with openings therein, which is rigidly connected to the connection means, and which secondly has a rotor with openings therein which is rigidly connected to a rotating mount and against which the inlet and outlet of said treatment units are guided, and that the openings in the stator and rotor are matched to each other in their spatial position in such a way that the process line of the connection means necessary for the treatment is in each case connected, in relation to the rotation angle, to the inlet and outlet of said treatment unit located in the stopping stations concerned.

22. Device according to claim 3, further comprising a heat exchanger provided in that process line of the connection means which serves to recycle cooling media from said treatment units, which heat exchanger is connected on the exit side to a process line which guides a process medium to heat up the product to be treated.

* * * * *